(12) United States Patent
Grossman et al.

(10) Patent No.: US 7,048,724 B2
(45) Date of Patent: May 23, 2006

(54) DEVICE FOR WITHDRAWING BODY FLUIDS

(75) Inventors: Phillip Grossman, Lakewood, CO (US); Warren Erickson, Lafayette, CO (US); Paul Burek, Centennial, CO (US); Bonnie Vivian, Evergreen, CO (US)

(73) Assignee: Denver Biomedicals, Inc., Golden, CO (US)

( * ) Notice: Subject to any disclaimer, the term of this patent is extended or adjusted under 35 U.S.C. 154(b) by 489 days.

(21) Appl. No.: 10/321,711

(22) Filed: Dec. 17, 2002

(65) Prior Publication Data

US 2004/0116902 A1    Jun. 17, 2004

(51) Int. Cl.
*A61M 1/00* (2006.01)

(52) U.S. Cl. ...................................... 604/319
(58) Field of Classification Search ............... 604/119, 604/319, 317, 540, 35, 73, 75, 411–415
See application file for complete search history.

(56) References Cited

U.S. PATENT DOCUMENTS

| 3,659,587 | A | * | 5/1972 | Baldwin | 600/577 |
| 4,246,899 | A | * | 1/1981 | Loseff | 604/97.02 |
| 4,275,731 | A | * | 6/1981 | Nichols | 604/319 |
| 4,306,557 | A | * | 12/1981 | North | 604/119 |
| 4,706,830 | A | * | 11/1987 | Wareing | 215/365 |
| 5,033,476 | A | * | 7/1991 | Kasai | 600/577 |
| 5,067,950 | A | * | 11/1991 | Broadnax, Jr. | 604/317 |
| 5,597,536 | A | * | 1/1997 | Mayer | 422/103 |
| 6,024,731 | A | * | 2/2000 | Seddon et al. | 604/317 |
| 6,261,276 | B1 | * | 7/2001 | Reitsma | 604/319 |

* cited by examiner

*Primary Examiner*—Sharon Kennedy
(74) *Attorney, Agent, or Firm*—Gibson, Dunn & Crutcher LLP; Stanley J. Gradisar

(57) ABSTRACT

An apparatus and method for draining fluid from a patient. A drainage line is connected to a vacuum bottle. The vacuum is transferred into the drainage line by piercing a seal over the bottle mouth. The indicator in the form of a collapsible bulb or other deformable element confirms the presence of the vacuum at the time of use.

27 Claims, 7 Drawing Sheets

DEVICE FOR WITHDRAWING BODY FLUIDS

FIELD OF THE INVENTION

The present invention relates to the field of medical devices and, in particular, to a device useful for withdrawing body fluids in procedures such as paracentesis and thoracentesis.

BACKGROUND

Body fluids may need to be withdrawn from a patient in the course of medical treatment. Two common medical procedures requiring fluid removal are thoracentesis and paracentesis.

In paracentesis, peritoneal fluid is aspirated from the abdomen. Typical patients have tense ascites resulting from liver disease and portal hypertension, which may cause discomfort, respiratory distress, and the formation and rupture of umbilical hernias. Paracentesis has been observed to provide quick and effective relief with few adverse side effects. Other treatment options, such as the use of diuretics, are available, but may not provide as effective relief as paracentesis. Additionally, many patients with ascites have renal impairment and cannot use the high doses of diuretics necessary to effectively treat the ascites. See "Large-Volume Paracentesis in Nonedematous Patients with Tense-Ascites: Its Effect on Intravascular Volume," Pinto et al., *Hepatology*, Vol. 8, No. 2, pp. 207–210, 1988. Relatively large volumes of fluid, such as five liters, may be withdrawn from a patient during one paracentesis procedure.

Many existing devices are capable of performing paracentesis. At its simplest, a paracentesis device need only include a hollow needle with one end inserted into the patient and the other end attached to a negative pressure device, such as a syringe or vacuum bottle. However, more specialized devices have been developed to allow safer, more comfortable, and more sanitary paracentesis. These devices may allow for body fluid to be dispensed into at least two containers, so that one container may be filled with fluid for diagnostic purposes and the other container may be filled with waste fluid. Another development has been the use of Kuss or Verres type needle assemblies, where a blunt drainage needle is attached to a retractile sharp introducer needle. This reduces the likelihood of the sharp needle damaging internal tissue during paracentesis. A further development is to drain body fluid through a blunt-tipped catheter introduced by a sharp introducing needle, which allows the sharp needle to be removed from the patient after a relatively quick introduction process and avoids the prolonged presence of a sharp needle in the body of the patient.

Problems may arise when drainage is diverted from one container to another if the drainage system is not airtight. Air could contaminate a sample or enter the body of the patient and cause injury. Known devices that are meant to be airtight have tubes and multiple containers attached to the devices which make the devices cumbersome and somewhat difficult to insert into the patient. Also, known devices require manipulation of a manual valve, such as a stopcock to work effectively. If the stopcock is not set at the proper setting, the device may admit air into the patient or otherwise malfunction. Problems also may arise in devices which allow a needle assembly to be withdrawn. Air must be prevented from entering the patient when the fluid is withdrawn. Also, body fluid must be prevented from leaking out of the device through the space formerly occupied by the needle assembly.

Thoracentesis is a procedure similar to paracentesis, except that effusion fluid is withdrawn from the pleural region instead of the abdomen. Normally, the pleural space contains approximately 5 to 20 ml of fluid. The fluid is the result of the hydrostatic-onctotic pressure of the capillaries of the parietal pleura. The turnover of the fluid in the pleural space is normally quite rapid, so that 5 to 10 liters of fluid move through the pleural space each day. A disruption in the balance between the movement of fluid into the pleural space and the movement of fluid out of the pleural space may produce excessive fluid accumulation in the pleural space. Pleural effusion is particularly common in patients with disseminated breast cancer, lung cancer or lymphatic cancer and patients with congestive heart failure, but also occurs in patients with many other forms of malignancy.

Pleural effusion may cause dyspnea, coughing, and chest pain, which diminish a patient's quality of life. Although pleural effusion typically occurs toward the end of terminal malignancies, such as breast cancer, it occurs earlier in other diseases. Therefore, relieving the clinical manifestations of pleural effusion is for real and extended advantage to the patient. For example, non-breast cancer patients with pleural effusion have been known to survive for years. See "Pleural Effusion in Cancer Patients," Izbicki et al., *Cancer*, October 1975, p. 1511.

There are several treatments for pleural effusion. If the patient is asymptomatic and the effusion is known to be malignant or paramalignant, no treatment may be required. Pleurectomy and pleural abrasion are generally effective in obliterating the pleural space, thus controlling the malignant pleural effusion. However, pleurectomy is a major surgical procedure associated with substantial morbidity and some mortality. Chemotherapy is generally disappointing; however, it may produce good responses for patients with lymphoma, breast cancer, or small-cell carcinoma. Another approach is to surgically implant a chest tube. However, such a tube is painful to the patient, both when it is inserted and during the time that it remains in the pleural space. Improvements on the traditional chest tube are described in U.S. Pat. No. 5,484,401, commonly owned with the present application.

Despite other treatment options, thoracentesis remains the most common approach to removing pleural fluid. However, thoracentesis poses the danger of causing pneumothorax, a collapsed lung. Pneumothorax can be caused directly by puncturing a lung with a needle assembly or catheter tip or indirectly by allowing air to enter the pleural space. Normally, the pleural space is at negative pressure relative to the atmosphere, which helps keep the lungs expanded. If the atmosphere is allowed to communicate with the pleural space, the pleural space may no longer be at negative pressure and pneumothorax may result.

Thoracentesis devices have been developed to reduce the risk of pneumothorax and other similar problems that may result from the procedure. In general, these devices incorporate similar protections as do paracentesis devices. For example, U.S. Pat. No. 4,447,235 by Clark discloses a thoracentesis device with a catheter introduced by a removable needle assembly, with a valve that closes upon removal of the needle assembly. The purpose of the valve is to prevent air from entering the body of the patient. U.S. Pat. Nos. 4,784,156, 4,832,044, 4,840,184, and 4,844,087 by Garg disclose similar devices with a manual valve that may be closed after withdrawal of the needle assembly. However, none of the previous devices allow for a truly fail-safe operation, as various valves must be properly set by the operator when changing from one drain port to another or when withdrawing the introducing needle assembly from the patient. Also, care must be taken to avoid accidental withdrawal of the introducing needle assembly, as in the disclosed devices where the needle assembly is not firmly attached to the remainder of the device. Further, the disclosed valves that allow for catheter drainage after removal of an introducing needle assembly rely on a single contact point. Due to the possibly dire consequences of a valve failure, such valves may not produce acceptably safe thoracentesis.

A Verres-type needle assembly that may be used for thoracentesis is disclosed in U.S. Pat. No. 5,334,159 by Turkel. While this reduces the risk of pneumothorax due to lung puncture, the Turkel device does not improve the safety of thoracentesis when the introducing needle assembly is withdrawn or solve the problems associated with multiple drainage ports. Thus there is a need for a safer and more reliable device that may be used for paracentesis and thoracentesis. Another device is described in U.S. Pat. No. 5,725,906, issued Mar. 10, 1998.

Other difficulties with existing systems relate to manufacturing, storing and using the vacuum element. Syringes are sometimes used to generate the vacuum, but syringes are somewhat complicated to manufacture and use. An alternative vacuum source is a vacuum bottle. In that approach, a vacuum is created in an air-tight bottle at the manufacturing stage, and then the bottle is sealed. The bottle is then tapped at the time of use so that the vacuum can be applied to a drainage line to remove the undesired body fluids.

This is quite ingenious in concept but somewhat difficult to implement. There is always some risk that the vacuum will be lost in transit before use, either by leaks, fractures or just air permeating through a plastic wall. Moreover, the loss of vacuum is not necessarily apparent to the user; a bottle with a perfect vacuum inside looks no different than a bottle of air. Another problems is in tapping the bottle. This requires a system that pierces a vacuum seal but does not allow air to enter the bottle, except through the draw line. Such a system should be easy to operate but not susceptible to accidental operation.

The contents of each document referred to herein is hereby incorporated by reference, although it is noted that such documents are not admitted to be prior art and are only referenced as they may be helpful to an understanding and appreciation of the present invention.

SUMMARY OF THE INVENTION

The present invention is a device and method for withdrawing body fluid. It is especially useful in paracentesis and thoracentesis.

In a preferred embodiment, an apparatus includes an evacuated bottle. The bottle is preferably evacuated at the manufacturing facility for the apparatus. Communication between the bottle and a fluid drainage tube is then established at the site of use for the apparatus. The drainage tube (or, more precisely, a needle or catheter connected thereto) is inserted into a fluid space in the patient in the conventional manner or otherwise, so that the vacuum in the bottle draws fluid from the patient into the drainage tube and into the bottle.

An important aspect of the invention, among others, is the manner of establishing communication between the vacuum bottle interior and the drainage tube lumen. In a preferred embodiment, the drainage tube terminates at its proximate end in a spike. The spike is held in position at the mouth of the bottle. Covering and closing the mouth of the bottle is an impermeable frangible seal. Communication between the drainage tube lumen and the vacuum of the bottle interior is established by pressing the spike into the frangible seal to pierce the seal. The surrounding structure adjacent the bottle mouth maintains the various elements in the desired configuration with respect to one another.

In another preferred embodiment, the drainage line terminates at a stopcock valve at the proximate end. The valve in turn is connected to the bottle and serves to seal the bottle interior vacuum. Communication between the bottle interior vacuum and the drainage line lumen is established by simply opening the value. In place of the valve, may be a simple slide clamp. The clamp clamps onto the drainage line to isolate the drainage line lumen from the bottle interior vacuum during packaging, shipping and storage. Removing, or unsliding, the slide clamp establishes such communication at the time of use.

Another important aspect of the invention, among others, is the manner of verifying the integrity of the vacuum in the bottle interior at the time of use. In one preferred embodiment, this is accomplished through a tubular fitting on the spike. The fitting has one end in communication with the spike interior and an opposite end in communication with a flexible bulb. In its natural state, the bulb is rounded. As mentioned, the spike is used to pierce the frangible seal at the time of use, thereby establishing communication between the bottle interior and the drainage tube lumen. Because the tubular fitting is also in communication with the spike interior, this also establishes communication between the tubular fitting interior and the bottle interior. If the bottle interior vacuum is properly intact, this vacuum will consequently be established into the bulb at the opposite end of the tubular fitting. The differential pressure between the vacuum in the bulb interior and the atmospheric pressure outside the bulb will thus collapse the bulb. This collapse is readily apparent to the user, and serves as an indicator that the vacuum is intact.

On the other hand, if the vacuum in the bottle interior is not properly intact, i.e. air has leaked into the bottle, then no vacuum or insufficient vacuum will be transferred from the bottle interior to the bulb interior. The bulb will then fail to collapse, and thereby fail to confirm that the vacuum is intact. Of course, the threshold for bulb collapse can be varied by appropriate use of materials and configurations, as desired, to serve properly the indicator function.

Another way to confirm that the vacuum in the bottle interior is sufficiently intact relies on a bottle cap that surrounds the mouth of the bottle outside the frangible seal. The cap is of a certain rounded shape in its normal, undistended state. The cap defines a space between the cap and the frangible seal of the bottle that separates the bottle vacuum from the spike and drainage tube lumen. Piercing the frangible seal with the spike establishes communication between the bottle interior and the space, thereby transferring the vacuum into that space. The differential pressure between the vacuum in that space and the atmosphere pressure outside the cap causes a partial collapse of the cap. That partial collapse serves as the indicator that the vacuum is partially intact. As in the bulb embodiment described above, the degree of collapse can be controlled by varying the materials and configurations.

The elements that serve to verify the integrity of the vacuum prior to use can also serve another function. During use, the vacuum gradually diminishes as the bottle fills with liquid. At some point, the vacuum becomes insufficient to perform the desired function of drawing fluid out of the patient. The elements indicating an insufficient vacuum prior to use will also indicate an insufficient vacuum at that point as well. This serves to indicate to the user that the bottle should be replaced with a fresh one.

The risk that the spike accidentally pierces the frangible seal, to lose the vacuum, prior to the time of use can be minimized with appropriate safety devices. In one preferred embodiment, the safety device is a clip that clips over the neck formed by the spike between the bottle mouth and a flange on the drainage line. So long as the clip is in place, any force urging the spike toward the frangible seal is transferred through the clip so that the spike cannot actually reach the frangible seal. At the time of use, the clip is simply removed to allow the spike to pierce the frangible seal in the manner described above.

DETAILED DESCRIPTION OF A PREFERRED EMBODIMENT

Figure 1:
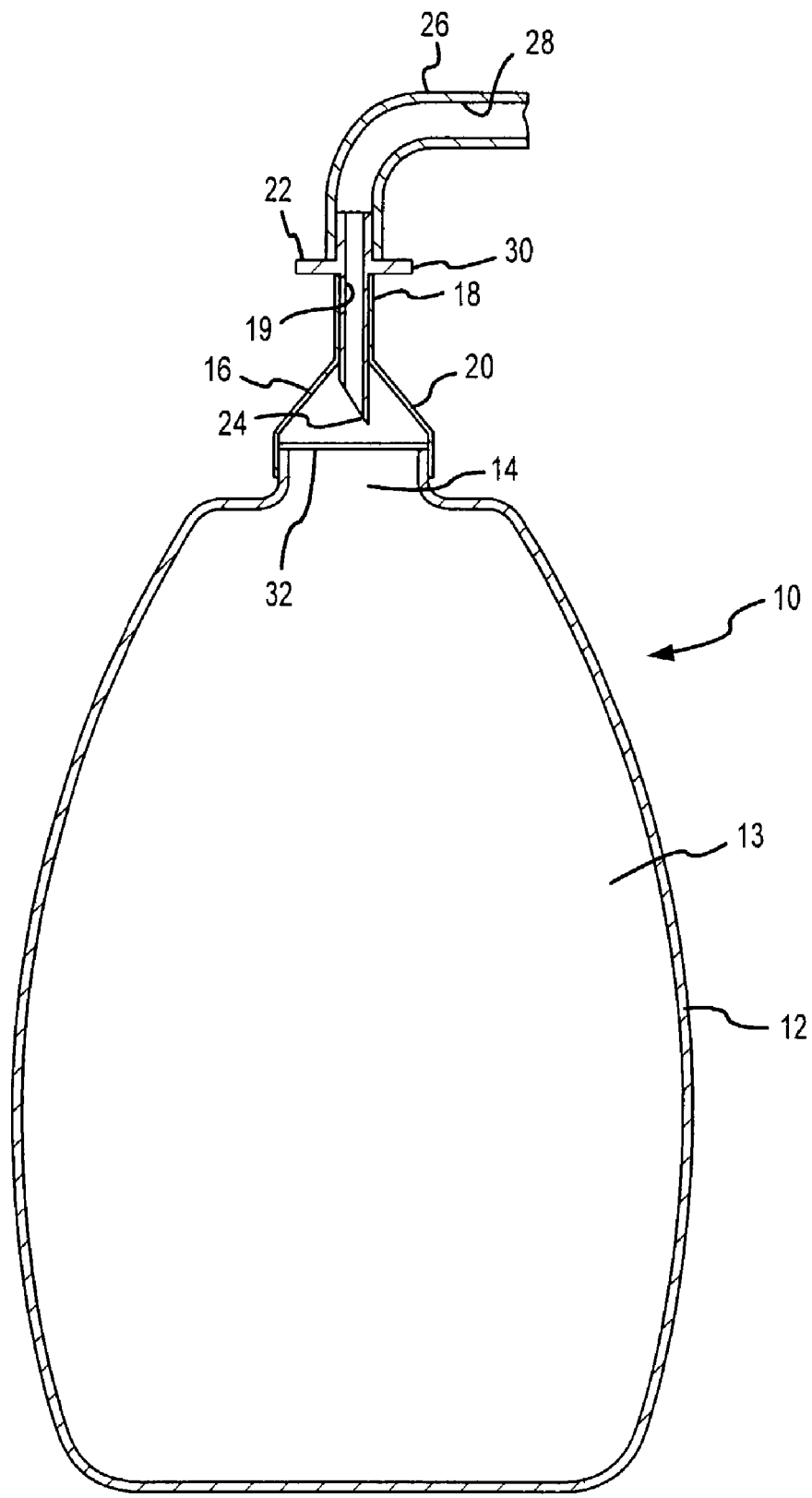
FIG. 1 shows a preferred embodiment of a device f or withdrawing body fluid of the present invention in a partial sectional view.

FIG. 1 shows a preferred embodiment of the invention 10 in a partial sectional view. The invention includes a bottle 12 having a mouth area 14. Covering the mouth area 14 is an elastomeric cap 16 having a sleeve 18 at the upper end and a widened body 20 at the lower end. The sleeve 18 of the elastomeric cap 16 receives a spike 22 in a substantially air tight seal between the spike 22 exterior surface and the lumen of the sleeve 18.

The lower end of the spike 22 terminates in a point 24. The upper end of the spike 22 receives a drainage line 26 having a lumen 28 therethrough. As in the connection between the spike 22 and the sleeve 18 of the elastomeric cap 16, this connection between the spike 22 and the drainage line 26 is preferably substantially air-tight. The spike 22 may also include a circumferential flange 30 to assist in manipulating the spike 22 in relation to the bottle 12 in the manner described below. Extending through the spike 22 is a spike lumen 19.

Sealing a vacuum in the bottle interior 13 is a frangible seal 32 that covers the mouth area 14 of the bottle 12. The frangible seal is preferably foil, mylar or other substantially air-tight material, attached to the edges of the mouth area 14 of the bottle 12 to substantially prevent air from leaking into the bottle interior 13 to spoil the vacuum therein. This attachment can be accomplished by heat-sealing (as in, for example, direct heat, induction heat or vibration generated heating processes) or by gluing or adhesion.

The invention 10 may be packaged and shipped in a form that includes the bottle 12 sealed by the frangible seal 32, and with or without the other elements. More specifically, the drainage line 26 may be attached to the rest of the assembly at the time of use, or not. Alternatively, both the spike 22 and drainage line 26 may be attached to the assembly at the time of use, or not. Or the drainage line 26, spike 22 and elastomeric cap 16 may be attached to the assembly at the time of use, or not. The important point is that the bottle is evacuated beforehand.

To use the device, it is assembled completely, if not already assembled completely. Then the drainage line 26 distal end (not shown in FIG. 1) is attached to a needle or catheter that is placed into a fluid space in the patient using conventional or non-conventional medical techniques. For example, the drainage line 26 distal end can be placed in the pleural space to remove excess pleural fluid by means of a needle or catheter.

Then the spike 22 is pushed toward the bottle 12 by applying a downward force to the flange 30. This deforms the elastomeric cap 16 widened body 20, which maintains the substantially air-tight seal between the elastomeric cap 16 sleeve 18 and the spike 22. The spike point 24 meets and pierces the frangible seal 32, thereby transferring the vacuum from the bottle interior 13 into the space defined by the elastomeric cap 16 (or, more precisely, thereby drawing nearly all the small quantity of air from the space into the bottle interior to establish a vacuum in that space). This vacuum also extends through the spike lumen 19 and into the drainage line lumen 28. The effect is to draw fluid from the distal end of the drainage line 26, through the drainage line 26 toward the bottle 12, through the spike lumen 19 and into the bottle 12.

The rate of fluid withdrawal, and the magnitude of the vacuum applied to the patient, can be managed by using a clamp on the drainage line 26. Opening the clamp slightly will produce a relatively modest vacuum at the drainage line 26 distal end and a relatively slow rate of fluid withdrawal, while opening the clamp more will produce a greater vacuum and faster rate of withdrawal.

As mentioned, it may be important to be able to verify at a glance that the vacuum in the bottle interior 13 is intact before using the device. In the embodiment shown in FIG. 1, this can be accomplished by the appearance of the elastomeric cap 16. In its normal undistended position, the elastomeric cap will have a given shape that is easily discernable to the user. As the spike 22 pierces the frangible seal 32 to transfer the bottle 12 vacuum into the space defined by the elastomeric cap 16, atmospheric pressure on the exterior of the elastomeric cap 16 will tend to partially collapse it. This partial collapse will thus be apparent to the user, thereby verifying the bottle interior 13 vacuum.

As also mentioned above, the vacuum indicator elements also serve to indicate a loss of vacuum over the course of the procedure. More specifically, the bottle gradually fills as fluid is drawn out of the patient, through the drainage line and into the bottle. This filling of the bottle of course lessens the vacuum, i.e., it increases the pressure to approach atmospheric. This loss of vacuum and resulting diminution in fluid flow could be mistaken for a sign that all the desired fluid has been withdrawn from the patient. The outcome would then be an incomplete procedure. This is prevented by the indicator elements. If the vacuum becomes insufficient over the course of the procedure, the indicator elements will so indicate, just as they indicate if the vacuum is insufficient at the outset of the procedure.

Figure 2:
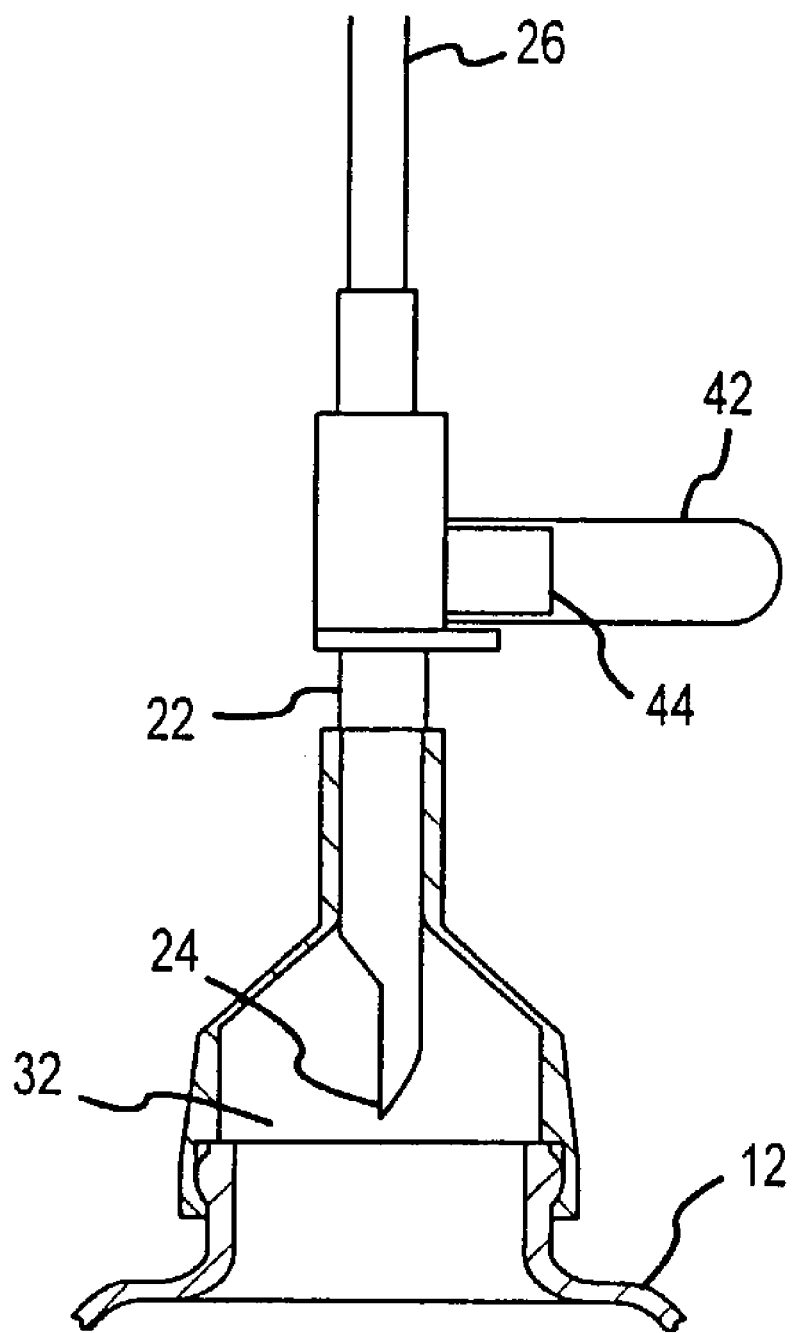
FIG. 2 shows an alternative embodiment of a device for withdrawing body fluid of the present invention in a partial sectional view having a collapsible bulb.

An alternative embodiment of the invention 10 is shown in FIG. 2, in which the system for verifying the integrity of the vacuum is more elaborate. The overall configuration is essentially the same as the preferred embodiment of FIG. 1 but with the addition of a collapsible bulb 42. The bulb 42 interior is in communication with the interior lumen of the spike 22 through a tubular fitting 44.

Before the spike 22 pierces the frangible seal 32 to transfer the vacuum into the spike 22 and drainage line 26 assembly, the bulb 42 is in its natural undistended state. After the spike 22 pierces the frangible seal 32 to transfer the vacuum into the spike 22 and drainage line 26 assembly, the differential pressure between the vacuum inside the bulb and the atmospheric pressure outside the bulb collapses or at least partially collapses the bulb. This collapse or partial collapse is readily apparent to the user, thereby confirming the integrity of the vacuum.

Figure 3:
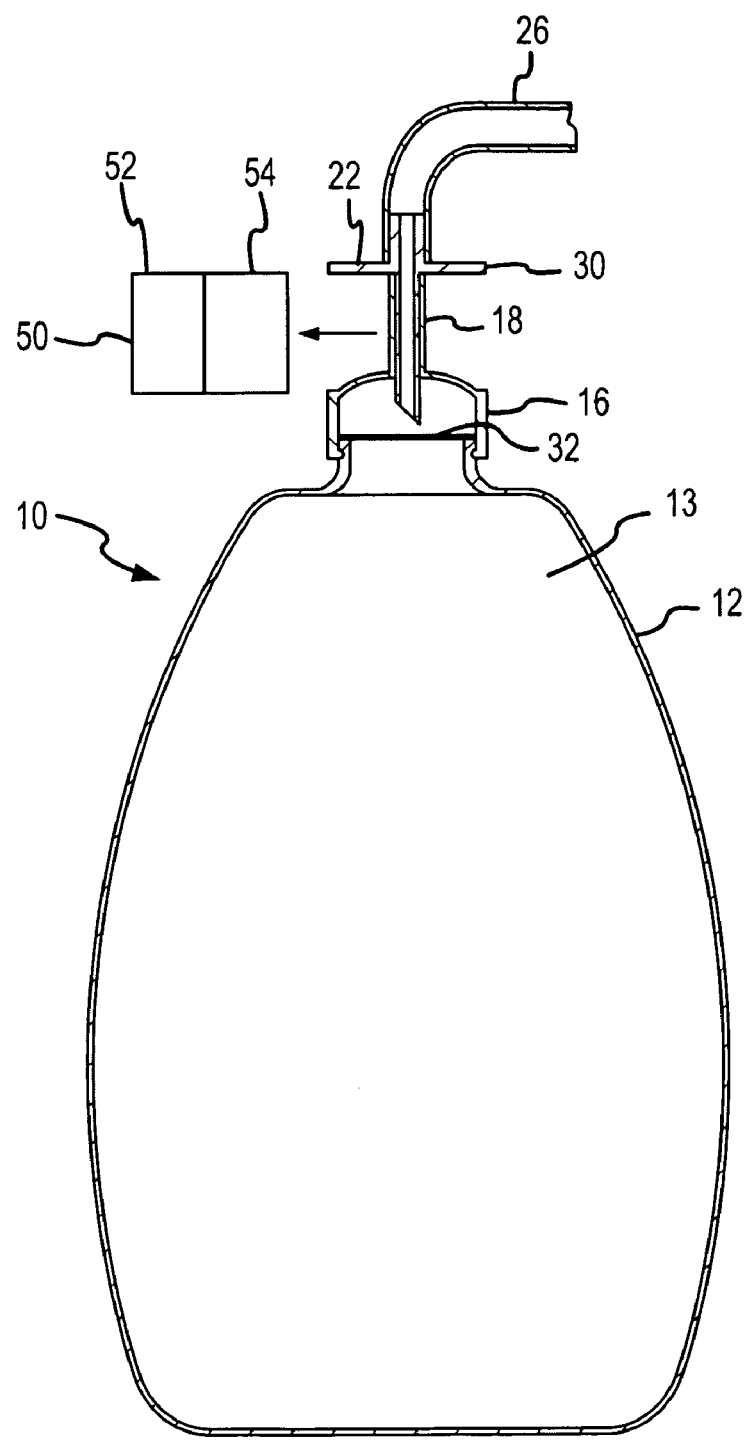
FIG. 3 shows another embodiment of a device for withdrawing body fluid of the present invention in a partial sectional view having a snap-in clip.

Another embodiment is depicted in FIG. 3. In this embodiment, the invention 10 also includes a clip 50 having a partially circumferential body 54 and a tab 52. The clip 50 is positionable over the body of the spike 22 between the flange 30 and the elastomeric cap 16. The dimensions and rigidity of the various elements is such that the clip snaps into place.

Before use, the clip 50 serves to prevent the spike 22 from being accidentally pressed downward to pierce the frangible seal 32 and destroy the vacuum. Any inadvertent downward force on the spike 22 is transferred through the clip body 54 into the elastomeric cap 16, rather than serving to move the spike 22 toward the frangible seal 32. At the time of use, the clip 50 is unsnapped from the rest of the assembly by pulling on the tab 52. Then the spike 22 can be moved toward the bottle 12 to pierce the frangible seal 32 in the manner described above.

It should be noted that the elastomeric cap 16 in the embodiment of FIG. 3 is configured somewhat differently than the elastomeric cap 16 in the embodiment of FIG. 1; the one of FIG. 3 is somewhat domed. The important point is that, whatever the shape, there is sufficient ability to accommodate the downward movement of the sleeve 18 as the spike 22 is moved downward to pierce the frangible seal 32. Also, the domed shape may be sufficiently flexible to collapse partially when the vacuum in the interior space defined by the elastomeric cap is established, to thereby serve as a vacuum integrity check.

Figure 4:
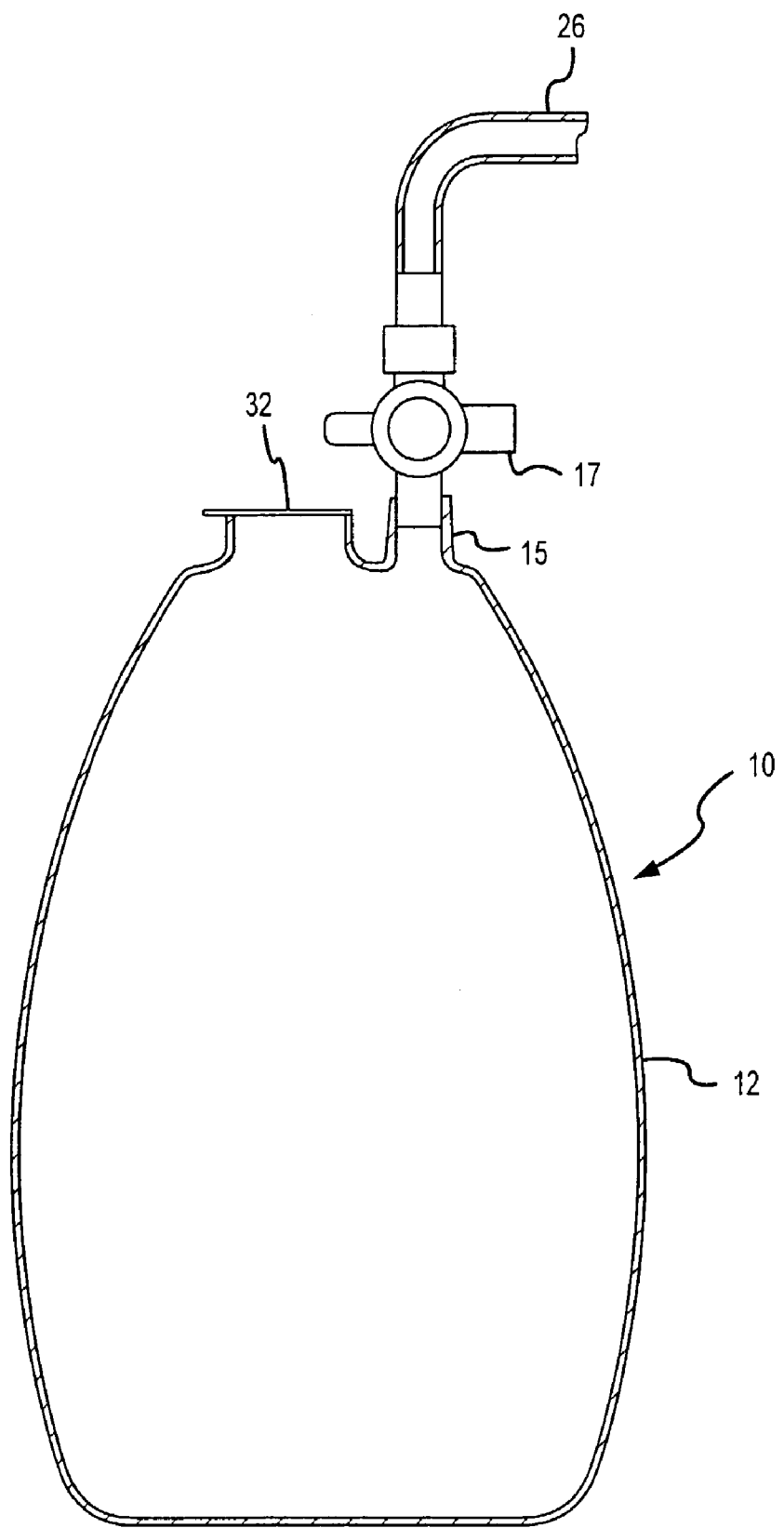
FIG. 4 shows another embodiment of a device for withdrawing body fluid of the present invention in a partial sectional view where a frangible seal acts as an indicator of vacuum integrity.

Yet another alternative embodiment is shown in FIG. 4. A bottle 12 has a flow port 15 which is stopped by a stopcock valve 17. The other end of the stopcock valve 17 is attached to the drainage line 26. At the time of use, the vacuum is transferred to the drainage line 26 by simply opening the stopcock valve 17. Of course, other types of valves or even a clamp may be used in place of a stopcock valve.

The embodiment of FIG. 4 also includes a frangible seal 32. However, in this embodiment, the frangible seal 32 is not used to transfer the vacuum from the bottle 12 to the drainage line 26. Instead, the frangible seal 32 serves simply as a port to empty the accumulated fluid in the bottle 12 after use. A second potential purpose for the frangible seal 32 is to act as a an indicator of vacuum integrity. The frangible seal can be of a material such that it dishes downwardly when there is a vacuum in the bottle. This dish-shape is apparent to the user, thereby confirming the presence of a vacuum in the bottle.

Figure 5:
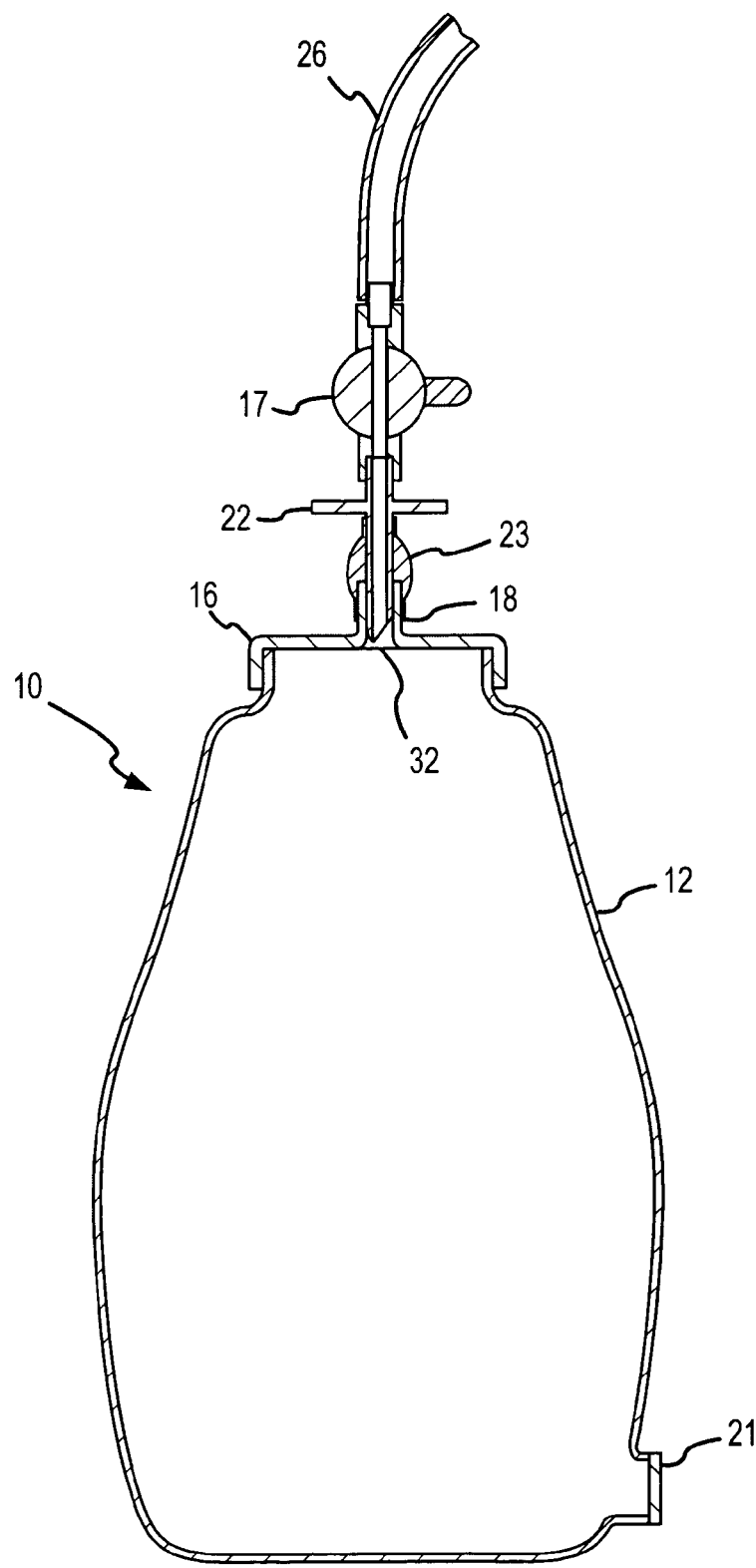
FIG. 5 shows another embodiment of a device for withdrawing body fluid of the present invention in a partial sectional view having an elastomeric surround.

FIG. 5 shows another alternative embodiment of the invention 10. The drainage line 26 is engaged with the vacuum bottle 12 through a stopcock or other valve 17 connected to the spike 22 positioned in a cap 16. The cap 16 may be threaded to mate with a threaded neck on the bottle, and sealed with an O-ring. Surrounding an upper sleeve 18 of the cap 16 and the lower portion of the spike 22 is an elastomeric surround 23. The elastomeric surround can perform two functions. First, it can allow the spike 22 to descend into the sleeve 18 of the cap 16 to pierce the frangible seal 32, thereby transferring the vacuum in the bottle to the drainage line 26. Second, the elastomeric surround 23 can serve to indicate the presence of the vacuum, by being constructed such that it partially collapses when the spike 22 pierces the frangible seal 32 to transfer the vacuum. Fluid may be drained from bottle 12 through an opening, port 21.

Figure 6:
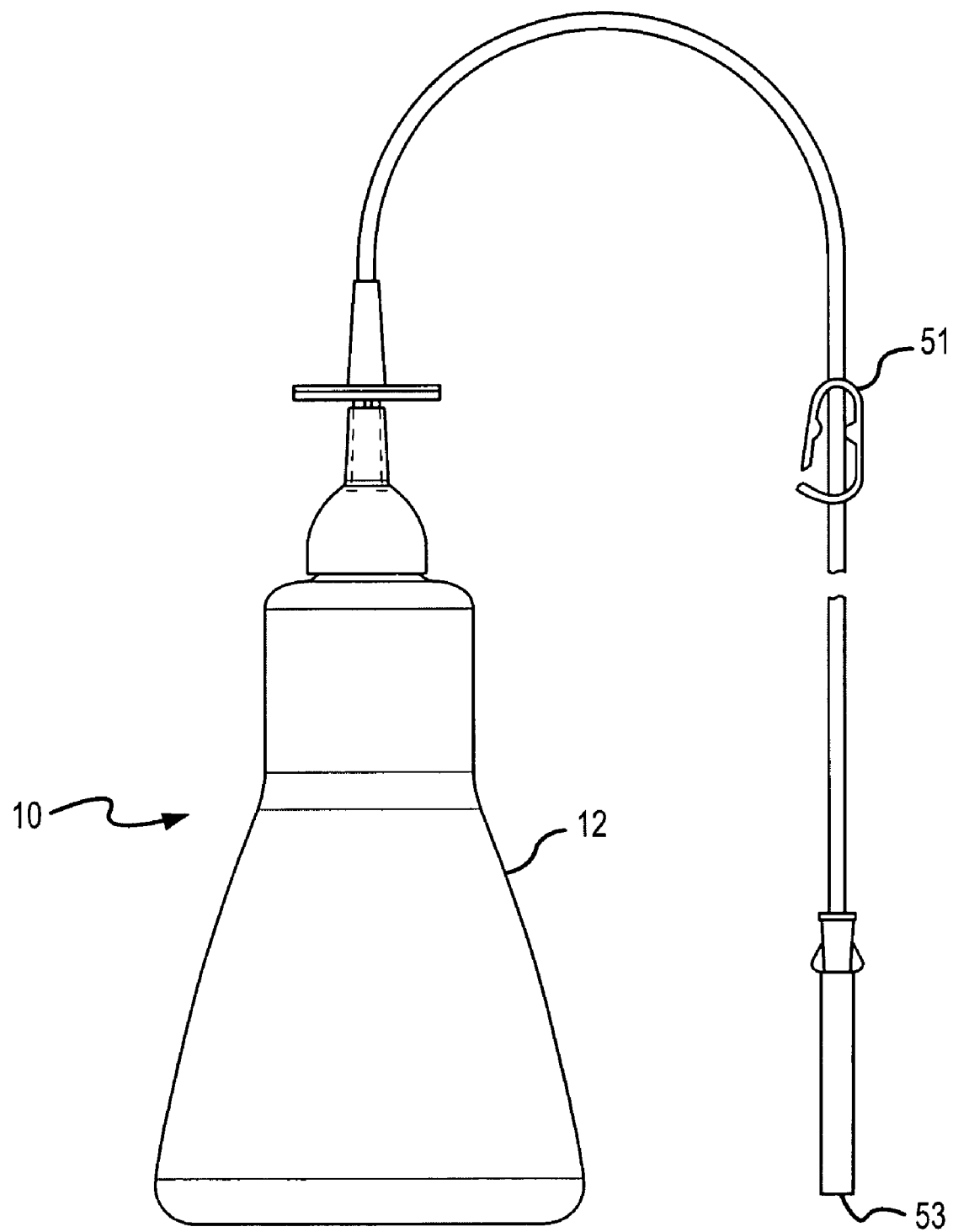
FIG. 6 shows an overall view of the present invention with a drainage line.

FIG. 6 shows an overall view of the invention 10 with a drainage line 26. It can be seen from this view that the drainage line 26 may be clamped with a pinch clamp 51, or a slide clamp or other clamp. The use of a clamp 51 on the flexible drainage line 26 allows greater control over the magnitude of the vacuum applied to the patient at the drainage line distal end 53 and the resulting rate of fluid withdrawal from the patient.

Figure 7:
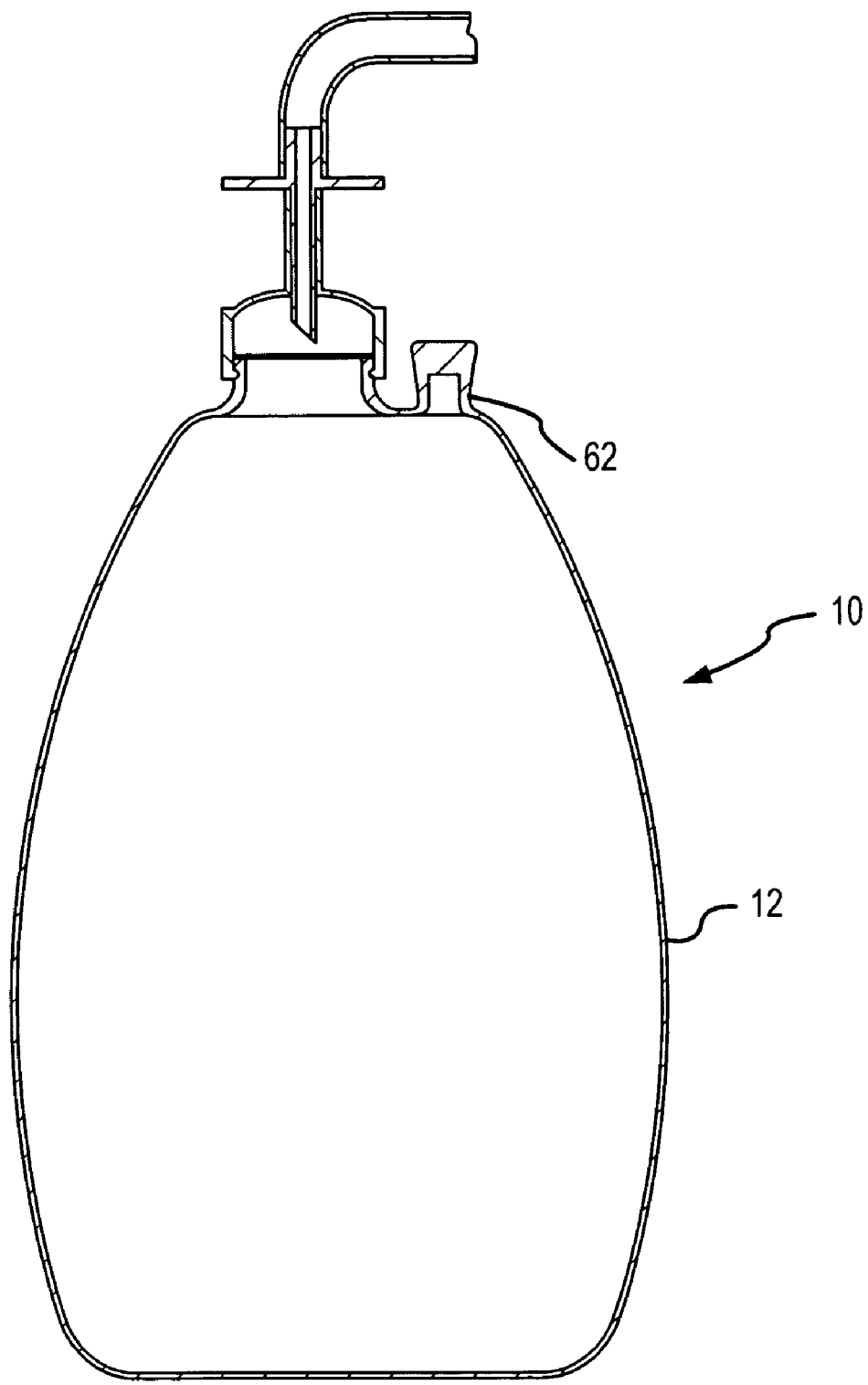
FIG. 7 shows another embodiment of a device for withdrawing body fluid of the present invention in a partial sectional view having an opening for producing a vacuum.

FIG. 7 shows yet another embodiment of the invention 10. In this embodiment, the vacuum in the bottle 12 is produced through an opening 62. This opening 62 is then swaged closed at the time of manufacturing. It should be noted that while the term "bottle" is used herein, such term should be construed to include any container.

What is claimed is:

1. An apparatus for removing fluid from a patient comprising:
   a container having an interior at a relatively low pressure, the container having a mouth covered by a seal;
   a drainage line connected to and extending away from the container;
   a piercing element having a spiked tube with a tubular body positioned proximate the mouth and capable of piercing the seal to transfer the low pressure from the container interior into the drainage line; and
   a container cap having an upper portion connected to the tubular body of the spiked tube and a lower portion covering the container mouth, the container cap being such that the spiked tube can be moved downward to pierce the seal, the container cap defining a space between a container cap wall and the seal;
   wherein the container cap has a first configuration when a pressure in the space is substantially atmospheric, and a second configuration when a pressure in the space is less than atmospheric, the second configuration being visibly different from the first configuration to confirm the low pressure in the container when the seal is pierced.

2. The apparatus of claim 1, wherein the seal is frangible.

3. The apparatus of claim 1, wherein the seal is of a material selected from the group consisting of foil and mylar.

4. The apparatus of claim 1, wherein the piercing element includes a flange to facilitate pressing the piercing element toward the seal.

5. The apparatus of claim 4, wherein the flange extends circumferentially around the piercing element.

6. The apparatus of claim 4, further comprising a safety element to prevent the piercing element from accidentally piercing the seal.

7. An apparatus for removing fluid from a patient comprising:
- a container having an interior at a relatively low pressure, the container having a mouth covered by a seal;
- a drainage line connected to and extending away from the container;
- a piercing element positioned proximate the mouth and capable of piercing the seal to transfer the low pressure from the container interior into the drainage line, wherein the piercing element includes a flange to facilitate pressing the piercing element toward the seal; and
- a clip that snaps over a portion of the piercing element to prevent accidentally piercing the seal.

8. The apparatus of claim 7, wherein the clip includes a body extending at least partly around the piercing element, and a tab to grasp the clip.

9. An apparatus for removing fluid from a patient comprising:
- a container having an interior at a relatively low pressure, the container having a mouth covered by a seal;
- a drainage line connected to and extending away from the container;
- a piercing element having a spiked tube with a tubular body positioned proximate the mouth and capable of piercing the seal to transfer the low pressure from the container interior into the drainage line; and
- a container cap having an upper portion connected to the tubular body of the spiked tube and a lower portion covering the container mouth, the container cap being such that the spiked tube can be moved downward to pierce the seal;
- wherein the container cap is sufficiently flexible to allow the lower portion to deform to accommodate downward movement of the spike.

10. The apparatus of claim 9, further comprising an indicator to indicate the low pressure in the container interior.

11. The apparatus of claim 10, further comprising a bulb, the bulb being at least partially collapsible and having an interior in communication with an interior of the container when the piercing element pierces the seal, whereby the bulb at least partially collapses when the low pressure of the container interior is transferred to the bulb interior upon piercing the seal.

12. The apparatus of claim 9, further comprising a valve positioned outside the container whereby opening the valve transfers the low pressure in the container to the drainage line.

13. The apparatus of claim 12, wherein the valve is a stopcock valve having one end attached to the drainage line.

14. The apparatus of claim 12, wherein the valve is a clamp on the drainage line.

15. The apparatus of claim 9, wherein the container includes a vacuum-introducing port that is swaged closed.

16. A method for draining fluid from a patient, comprising:
- establishing fluid communication between the patient and an interior lumen of a drainage line;
- attaching the drainage line to a container cap;
- attaching said container cap to a container at a mouth covered by a seal, said container having a relatively low pressure interior;
- moving a piercing element positioned in said container cap toward said mouth;
- piercing said seal with said piercing element and thereby transferring said low pressure from said container interior through said piercing element into said drainage line, wherein said container cap has a first configuration when a pressure in a space between a container cap wall and said seal is substantially atmospheric, and a second configuration when a pressure in said space is less than atmospheric, the second configuration being visibly different from the first configuration to confirm said low pressure in said container when said seal is pierced; and
- and allowing the fluid to drain from the patient to said interior of said container.

17. The method of claim 16, wherein said piercing element is a spiked tube and said seal is a frangible seal.

18. The method of claim 16, further comprising indicating a loss of low pressure as the fluid flows into said container.

19. The method of claim 16, wherein said container and said drainage line are connected by a valve, and further comprising opening said valve.

20. The method of claim 16 wherein said drainage line includes a clamp, and further regulating a rate of fluid transfer by adjusting said clamp.

21. The method of claim 16, further comprising draining the fluid from said container through an opening in said container.

22. A method for draining fluid from a patient, comprising:
- establishing fluid communication between the patient and an interior lumen of a drainage line;
- attaching said drainage line to a container cap, said container cap having an upper portion and a lower portion;
- attaching said container cap at said lower portion to a mouth of a container, said mouth covered by a seal, wherein said container has a relatively low pressure interior;
- moving a piercing element positioned in said container cap toward said mouth, said piercing element connected to an upper portion of said container cap; and
- piercing said seal with said piercing element and thereby transferring said low pressure from said container interior through said piercing element into said drainage line, wherein said container cap is sufficiently flexible to allow said lower portion to deform to accommodate movement of said piercing element.

23. The method of claim 22, further comprising the step of:
- allowing the fluid to drain from the patient to said interior of said container.

24. The method of claim 22, wherein said piercing element is a spiked tube and said seal is a frangible seal.

25. A method for draining fluid from a patient, comprising:
- establishing fluid communication between the patient and an interior lumen of a drainage line;
- attaching said drainage line to a container cap;
- attaching said container cap to a mouth of a container, said mouth covered by a seal, wherein said container has a relatively low pressure interior; and
- positioning a clip over the body of a piercing element between a flange of the piercing element and said container cap to prevent movement of said piercing element to accidentally pierce said seal on said mouth of said container.

26. The method of claim 25, further comprising the steps of:
- pulling on a tab of said clip in order to remove said clip from said body of said piercing element;

moving said piercing element toward said mouth;

piercing said seal with said piercing element and thereby transferring said low pressure from said container interior through said piercing element into said drainage line; and allowing the fluid to drain from the patient to said interior of said container.

27. The method of claim 25, wherein said piercing element is a spiked tube and said seal is a frangible seal.

* * * * *